United States Patent [19]

Shinkai et al.

[11] Patent Number: 5,231,196
[45] Date of Patent: Jul. 27, 1993

[54] CALIXARENE DERIVATIVES AND PROCESS FOR THE PREPARATION THEREOF

[75] Inventors: Seiji Shinkai; Tsutomu Matsuda; Takashi Arimura, all of Fukuoka; Kirosuke Kawabata; Kozo Tachibana, both of Hyogo, all of Japan

[73] Assignee: Daicel Chemical Industries, Ltd., Osaka, Japan

[21] Appl. No.: 627,637

[22] Filed: Dec. 14, 1990

[30] Foreign Application Priority Data

Sep. 13, 1990 [JP] Japan .................................. 2-224753

[51] Int. Cl.$^5$ .......................................... C07D 313/00
[52] U.S. Cl. .................................................. 549/354
[58] Field of Search ................. 549/354; 528/212, 217

[56] References Cited

U.S. PATENT DOCUMENTS 4,855,461  8/1989  Harris ..................... 549/354

FOREIGN PATENT DOCUMENTS 0279521  8/1988  European Pat. Off. ............ 549/354
0309291  3/1989  European Pat. Off. ............ 549/354

Primary Examiner—C. Warren Ivy
Assistant Examiner—Raymond Covington
Attorney, Agent, or Firm—Flynn, Thiel, Boutell & Tanis

[57] ABSTRACT

The present invention relates to an improvement in the process for preparing a calixarene derivative in which the rotation of its benzene units are hindered and which comprises replacing all or a part of the hydrogen atoms of the hydroxyl groups of a calixarene derivative represented by the general formula:

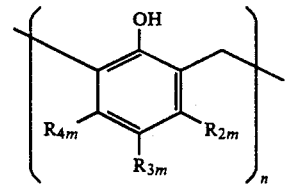

and is characterized by conducting the reaction in the presence of an alkaline earth metal. According to the present invention, an asymmetric calixarene derivative having a "cone" conformation can be selectively prepared by virtue of the template effect of the metal.

3 Claims, 4 Drawing Sheets

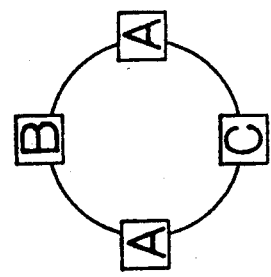
FIG. 3
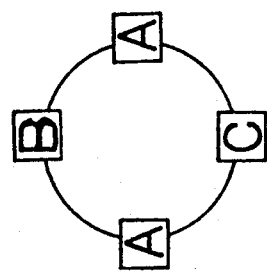
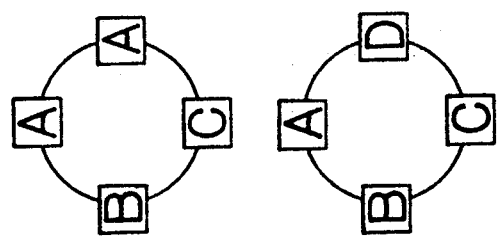 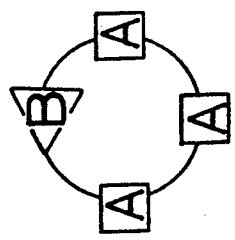
FIG. 1 FIG. 2
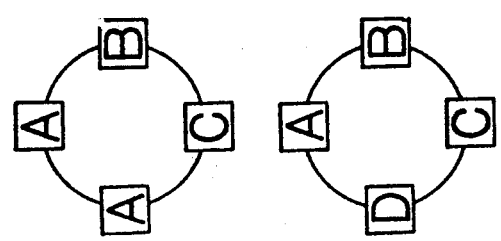 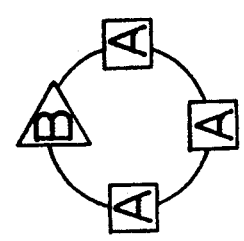

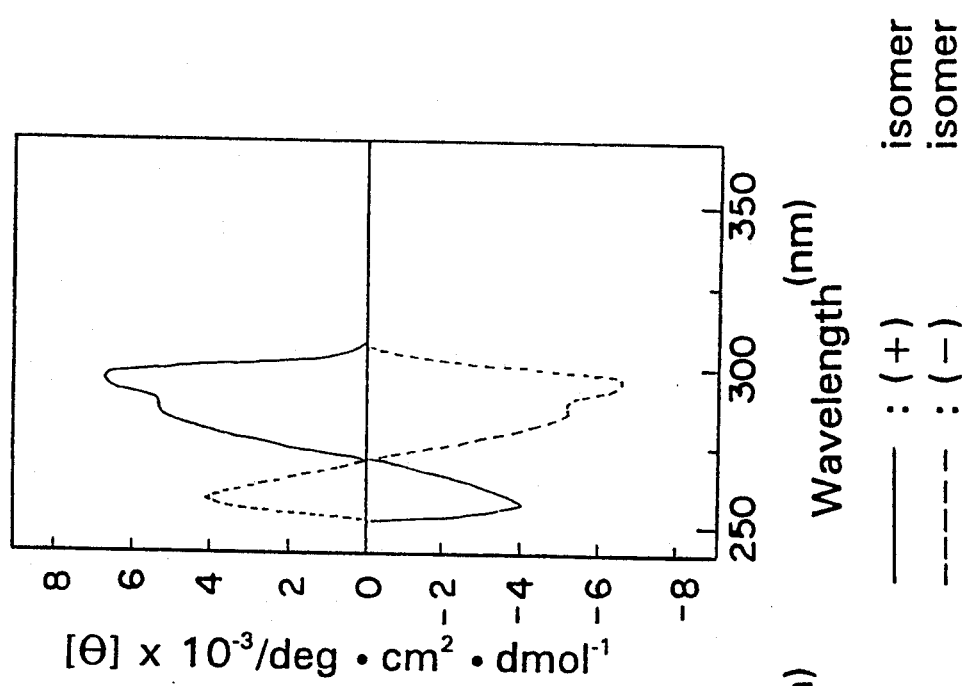
FIG. 11
FIG. 10
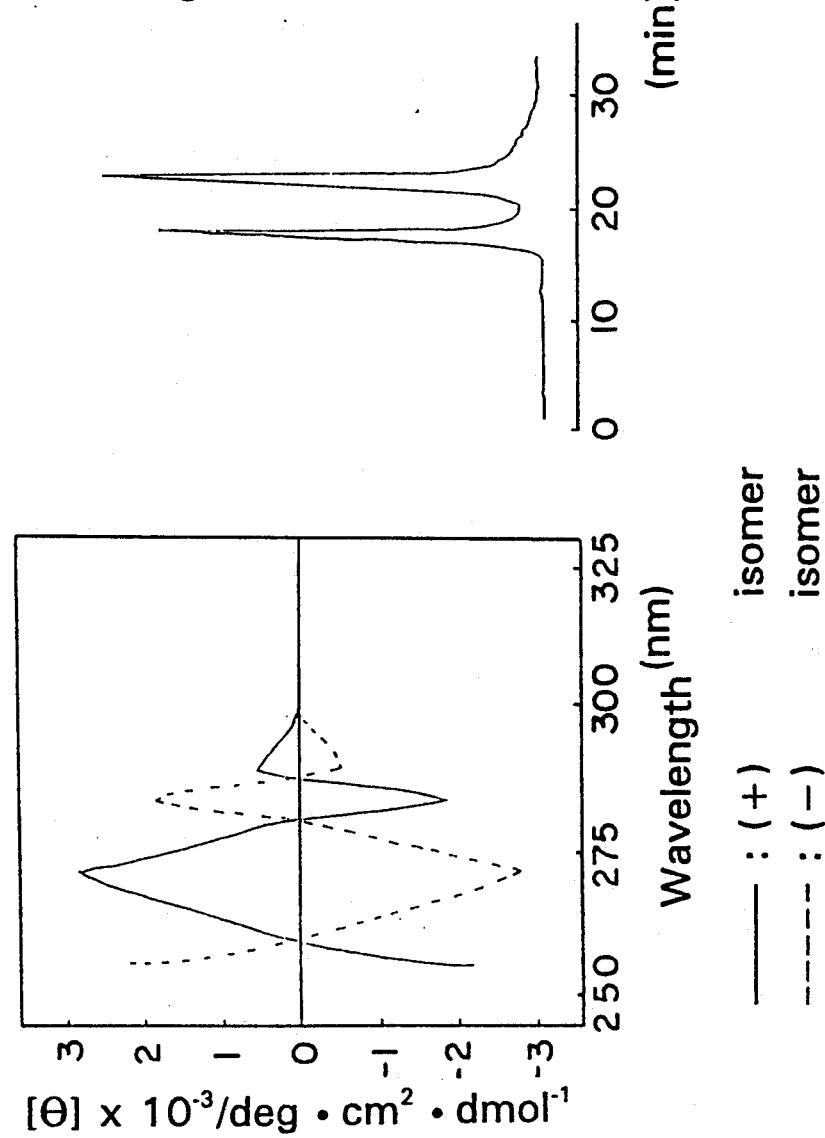
FIG. 9

CALIXARENE DERIVATIVES AND PROCESS FOR THE PREPARATION THEREOF

BACKGROUND OF THE INVENTION

1. Field of the Invention

The present invention relates to asymmetric calixarene derivatives and a process for the preparation of the same.

2. Description of the Prior Art

It has been found by C. D. Gutsche et al. that the reaction of a phenol with formaldehyde under suitable conditions gives cyclic tetrameric to octameric compounds, i.e., calixarenes (see, for example, J. Org. Chem., 43, 4905 (1978)). The benzene units of the calixarene each have such a freedom of causing conformational changes that they generally rotate at relatively high rates around room temperatures (see C. D. Gutsche et al., J. Am. Chem. Soc., 104, 2652 (1982)). Owing to this freedom, a calixarene is present as several conformational isomers. For example, a calix[4]arene is present as four conformational isomers, i.e., cone, partial cone, 1,2-alternate and 1,3-alternate. A calix[4]arene or a calix[5]arene generally takes a stable cone conformation owing to the rotation of the benzene units.

Meanwhile, it has been thought that a suitable derivative of a calixarene can possess an asymmetric structure. For example a calix[4]arene having at least three kinds of different benzene units, shown in FIG. 1, or at least one laterally unsymmetrical benzene unit, shown in FIG. 2, can possess an asymmetric strtucture. However, since such a calix[4]arene causes inversion owing to the rotation of its benzene units to give a racemization, the rotation of the benzene units must be hindered in order to obtain an optically active substance. It has been already known that the rotation of the benzene units of a calixarene can be hindered by converting a calixarene into a suitable derivative (see, for example, C. D. Gutsche et al., Tetrahedron, 39, 409 (1983)). However, when such a derivative is prepared by the process of the prior art, a mixture of various conformational isomers as described above is formed because of the hindrance to the rotation of the benzene units, and the isolation of a pair of optical isomers from the crude product is very difficult. Thus, neither a process for the effective preparation of a racemic modification of a calixarene derivative nor a process for the optical resolution thereof have been found as yet.

BRIEF DESCRIPTION OF THE DRAWINGS

FIGS. 1 to 3 are typical illustrations of the structure of the calix(4)arene derivative according to the present invention; FIG. 9 is circular dichroism spectra of the obtained optical isomers; FIG. 10 is a chromatogram of the optical resolution in Example 4; and FIG. 11 is circular dichroism spectra of the obtained optical isomers.

SUMMARY OF THE INVENTION

Figure 4:
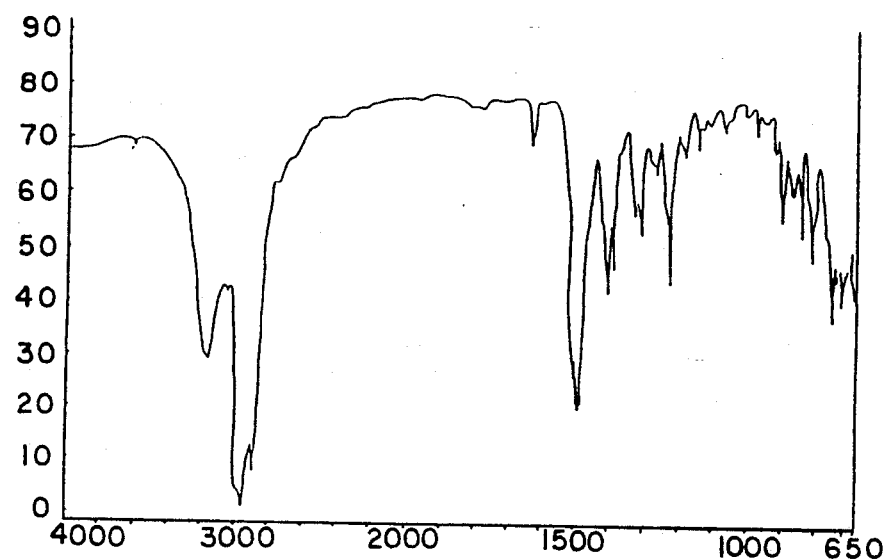
FIG. 4 is an infrared absorption spectrum of the calixarene derivative prepared in Example 1.

In order to solve the above problem, the inventors of the present invention have developed a process for the preparation of a calixarene derivative characterized by using an alkaline earth metal base such as barium hydroxide, calcium hydride or calcium hydroxide in the reaction of the hydroxyl groups of a compound represented by the general formula (2):

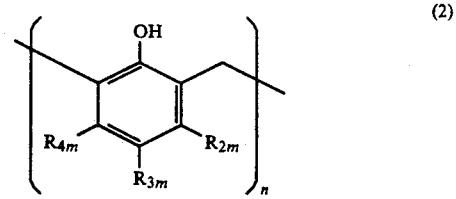

(2)

(wherein n is an integer of 4 to 12 preferably 4 to 8; m is an integer of 1 to n; and $R_{11}$ to $R_{1m}$, $R_{21}$ to $R_{2m}$ and $R_{31}$ to $R_{3m}$ each represent a hydrogen atom, a straight-chain or branched, saturated or unsaturated, acyclic or cyclic group having 1 to 20 carbon atoms which may contain a heteroatom, a substituted or unsubstituted aromatic group having 4 to 20 carbon atoms, or an aralkyl group having 5 to 20 carbon atoms), by which a calixarene derivative having a specific conformation called "cone" is selectively prepared by virtue of the template effect of the base, wherein the cone conformation being one characterized in that the hydroxyl groups or substituents therefor are all present on the same side of the ring structure. The present invention has been accomplished on the basis of this finding.

FIGS. 1 to 3 are typical illustrations of the structure of the calixarene derivative according to the present invention, wherein □ represents a laterally symmetrical benzene unit of a calix 4 arene; represents a laterally unsymmetrical benzene unit thereof and A, B, C and D are benzene units different from each other. For example, when the process of the present invention is applied to a case as shown in FIG. 2 wherein a calixarene derivative is not present as a racemic modification because of the rapid rotation of the benzene units though it has a structure which can exhibit asymmetry, the derivative is selectively induced into "cone"-type one hindered in the rotation of the benzene units, thus giving a racemic modification of a calixarene derivative.

The calixarene derivative of the present invention is one having an asymmetric structure and represented by the general formula (1):

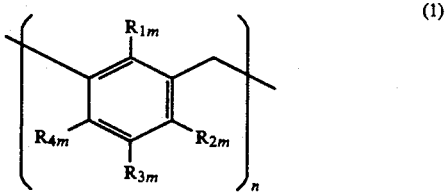

(1)

(wherein n is an integer of 4 to 12, preferably 4 to 8; m is an integer of 1 to n; and $R_{11}$ to $R_{1m}$, $R_{21}$ to $R_{2m}$, $R_{31}$ to $R_{3m}$ and $R_{41}$ to $R_{4m}$ represents a hydrogen atom, a straight-chain or branched, saturated or unsaturated, acyclic or cyclic group having 1 to 20 carbon atoms which may contain a heteroatom, a substituted or unsubstituted aromatic group having 4 to 20 carbon atoms, or an aralkyl group having 5 to 20 carbon atoms, with the proviso that they must be selected so as to have enough bulkiness to hinder the rotation of the benzene units around the ring, though they are not particularly limited in structure, and although the bulkiness needed to hinder the rotation varies depending upon the value of n, the rotation can be hindered when, for example, $R_{11}$ to $R_{14}$ are each a n-propyloxy group in a case wherein n is 4).

Although a calix(4)arene derivative having at least three kinds of benzene units can take an asymmetric structure as described above, the asymmetry is lost when the benzene units are arranged as shown in FIG. 3. Accordingly, the development of a process for the preparation of such a calixarene derivative without losing the asymmetry has been sought.

As a result of studies, the inventors of the present invention have developed a process for the preparation of an asymmetric calixarene derivative hindered in the rotation of its benzene units which comprises replacing all or a part of the hydrogen atoms of the hydroxyl groups of a calixarene derivative represented by the general formula (2):

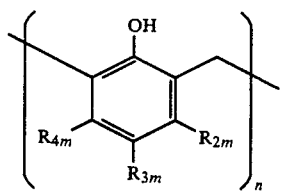

(2)

(wherein n is an integer of 4 to 12, preferably 4 to 8; m is an integer of 1 to n; and $R_{11}$ to $R_{1m}$, $R_{21}$ to $R_{2m}$, and $R_{31}$ to $R_{3m}$ each represent a hydrogen atom, a straight-chain or branched, saturated or unsaturated, acyclic or cyclic group having 1 to 20 carbon atoms which may contain a heteroatom, a substituted or unsubstituted aromatic group having 4 to 20 carbon atoms, or an aralkyl group having 5 to 20 carbon atoms) by a straight-chain or branched, saturated or unsaturated, acyclic or cyclic group having 1 to 20 carbon atoms which may contain heteroatom, a substituted or unsubstituted aromatic group having 4 to 20 carbon atoms, or an aralkyl group having 5 to 20 carbon atoms, characterized in that one kind of a conformational isomer is selectively prepared by conducting the reaction in the presence of an alkaline earth metal and that one to three bulky substituents are first introduced and the introduction of residual substituents is then conducted regioselectively. For example, when one bulky substituent B is first introduced into a calix(4)arene and two substituents A are then introduced thereinto, one of the substituents A is first introduced at a position diagonal to the substituent B owing to the steric effect of the substituent B and the other substituent A is then introduced at a position adjacent to the substituent B. Thus, a racemic modification as shown in the upper row in FIG. 1 is formed.

An asymmetric calixarene derivative represented by the above general formula (1) prepared by the above process can be optically resolved by bringing it into contact with an optically active polymer mainly constituted of a unit represented by the following general formula (3)

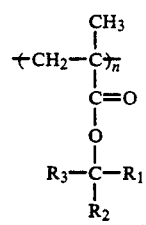

(3)

(wherein n is an integer of 20 or above and $R_1$, $R_2$ and $R_3$ may be the same or different from each other and each represent a substituted or unsubstituted aromatic group having 4 to 10 carbon atoms and which may contain a heteroatom), and having a specific rotation of at least 50° (in terms of absolute value), or a substance prepared by bonding an optically active group derived from an amino acid represented by the following general formula (4):

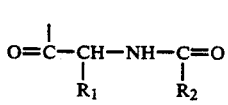

(4)

(wherein $R_1$ and $R_2$ each represent a straight-chain or branched, saturated or unsaturated, acyclic or cyclic group having 1 to 20 carbon atoms which may contain a heteroatom, a substituted or unsubstituted aromatic group having 4 to 20 carbon atoms, or an aralkyl group having 5 to 20 carbon atoms, with the proviso that R must be different from an

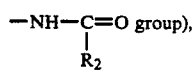

to a carrier

By the above optical resolution, an optically active calixarene derivative represented by the general formula (1):

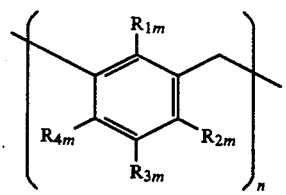

(1)

(wherein n is an integer of 4 to 12, preferably 4 to 8; m is an integer of 1 to n; and $R_{11}$ to $R_{1m}$, $R_{21}$ to $R_{2m}$, $R_{31}$ to $R_{3m}$ and $R_{41}$ to $R_{4m}$ each represent a hydrogen atom, a straight-chain or branched, saturated or unsaturated, acyclic or cyclic group having 1 to 20 carbon atoms which may contain a heteroatom, a substituted or unsubstituted aromatic group having 4 to 20 carbon atoms, or an aralkyl group having 5 to 20 carbon atoms, with the proviso that they must be selected so as to give a bulkiness enough to hinder the rotation of the benzene units around the ring, though they are not particularly limited in structure, and although the bulkiness enough to hinder the rotation varies depending upon the value of n, the rotation can be hindered when, for example, $R_{11}$ to $R_{14}$ are each a n-propyloxy group in a case wherein n is 4) can be prepared.

The compound of the invention can form an inclusion compound and therefore can be used for optical separation of another racemate. It has a corn-like structure. It has hydroxy groups which are alligned on the edge of its cylindrical structure and will eventually work to form a cationic coordination like crown ether compounds. It can include in its cylindrical structure an organic compound, like cyclodextrin. Moreover, it has many hydroxy groups and benzene rings which may easily have substituents thereon and therefore can be designed into derivatives providing intended physical properties. These possibilities will result in optical separation of many compounds and other applications.

DETAILED DESCRIPTION OF PREFERRED EMBODIMENTS

The present invention will now be described in more detail by referring to the following Examples.

Figure 5:
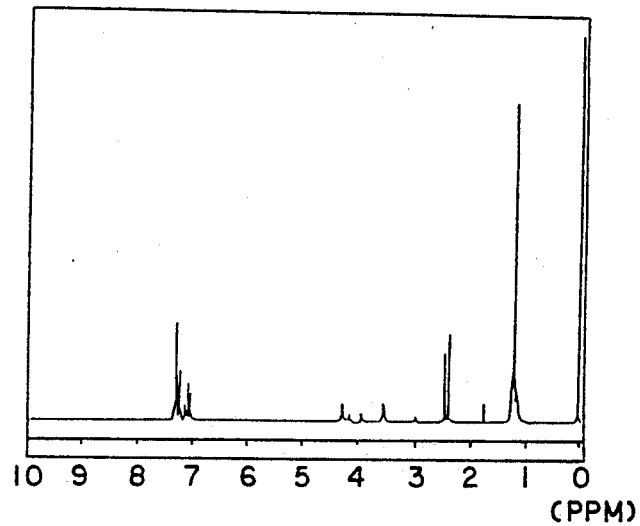
FIG. 5 is a nuclear magnetic resonance spectrum thereof.

EXAMPLE 1:

Synthesis of 4-methyl-5-isopropyl-11,17,23-tri-t-butyl-25,26,27,28-tetra-n-propyloxycalix[4]arene 120 ml of a solution of 3.28 g (9.76 mmol) of 2,6-bis(-bromomethyl)-3-methyl-4-isopropylphenol and 4.63 g (9.76 mmol) of 2,6-bis(2-hydroxy-5-t-butylphenylmethyl)-4-t-buthylphenol in distilled dioxane was dropped into 600 ml of distilled dioxane containing 10.0 ml (91.0 mmol) of titanium tetrachloride within high-degree dilution equipment over a period of 34 hours. After the completion of the dropping, the obtained mixture was cooled by allowing it to stand, followed by the addition of methanol. The resulting mixture was freed from the solvent by vacuum distillation and the obtained residue was dissolved in methylene chloride. The obtained solution was washed with water, dried over anhydrous sodium sulfate and filtered. 30 g of silica gel was added to the obtained filtrate and the obtained mixture was stirred to carry out absorption. The resulting mixture was extracted with methylene chloride by the use of a Soxhlet apparatus. The extract was freed from the solvent by vacuum distillation. The obtained residue (6.88 g) was purified by silica gel chromatography (benzene/hexane=1:1) to give a white solid (0.84 g, TLC: Rf=0.68, 0.52). This solid was recrystallized from toluene to give 575 mg (0.886 mmol) of 4-methyl-5-isopropyl-11,17,23-tri-t-butyl-25,26,27,28-tetrahydroxycalix[4]arene as a colorless prism. Yield : 9%, m.p : 265.5° to 266.0° C., TLC:Rf=0.68 (benzene/hexane=1:1). The infrared absorption spectrum of the product is shown in FIG. 4 and the nuclear magnetic resonance spectrum thereof is shown in FIG. 5.

|  | elemental analysis | |
|---|---|---|
|  | C % | H % |
| found | 82.33 | 8.50 |
| calculated[a] | 81.44 | 8.70 |
| calculated[b] | 82.66 | 8.70 |

[a] calculated as $(C_{11}H_{14}O)_4$
[b] calculated as a total of $(C_{11}H_{14}O)_4$ and toluene 0.35 g (0.539 mmol) of the product and 10.8 ml of dimethylformamide were placed in a nitrogen-purged flask, followed by the addition of 0.56 g (3.29 mmol) of barium oxide (purity : 90%) and 0.60 g (1.90 mmol) of barium hydroxide octahydrate. 2.91 ml (32.3 mmol) of propyl bromide was added into the flask. The obtained mixture was stirred at room temperature for 19 hours. 10 ml of a 5% aqueous solution of hydrochloric acid and 10 ml of water were added into the flask successively to precipitate a crystal. This crystal was extracted with chloroform. The obtained chloroform layer was separated, washed with water, dried over anhydrous sodium sulfate, and filtered. The filtrate was freed from the solvent by distillation to give a colorless transparent oil. Methanol was added to the oil to precipitate a white crystal. This crystal was purified with a large-scale TLC sheet to give 186 mg (0.246 mmol) of 4-methyl-5-isopropyl-11,17,23-tri-t-butyl-25-hydroxy-26,27,28-tri-n-propyloxycalix[4]arene in a yield of 45%. m.p.: 251.5° to 253.0° C.

The above product was reacted with n-propyl bromide in the presence of sodium hydroxide in a dimethylformamide/tetrahydrofuran mixture to give the title compound in a yield of 72%. m.p.: 163° to 164° C.

|  | elemental analysis | |
|---|---|---|
|  | C % | H % |
| found | 82.31 | 9.94 |
| calculated | 82.30 | 9.87 |

IR (Nujol)
$\nu_{C-O}$1130, 1220 cm$^{-1}$, $\nu_{OH}$ not observed, $\nu_{C=C}$1490 cm$^{-1}$, $\delta_{C-H}$880 cm$^{-1}$ NMR
(CDCl$_3$, 30° C.)$\delta$60.95–1.04(m, 15H, CH$_3$ in n-PrO and CH$_3$ in i-Pr), 1.01, 1.05, 1.06(s each, 9H each, t-Bu), 1.12(d, 3H, CH$_3$ in i-Pr), 1.89–2.06(m, 8H, C—CH$_2$—C in n-Pr), 2.12(s, 3H, 4-Me), 2.90(m, 1H, CH in i-Pr), 3.10, 3.11, 3.12, 3.37(d each, 1H each, Hendo in ArCH-2Ar), 3.69–4.03(m, 8H, OCH$_2$), 6.62, 6.68, 6.69, 6.73, 6.74, 7.26(broad, 7H, ArH).

EXAMPLE 2

Synthesis of 5,11,17,23-tetra-t-butyl-25-(2-pyridylmethoxy)-26,27-di-n-propyloxycalix[4]arene 253 mg (1.54 mmol) of α-chloromethylpyridine hydrochloride and 124 mg (3.08 mmol) of sodium hydride (60%) were added to 20 ml of toluene. The obtained mixture was stirred at room temperature for 30 minutes, followed by the addition of 500 mg (0.77 mmol) of p-t-butylcalix[4]arene. The obtained mixture was stirred in an oil bath kept at 70° C. for 20 hours, treated with methanol and distilled in a vacuum to remove the toluene. The residue was extracted with chloroform/water. The chloroform layer was separated, washed with water, dried over anhydrous sodium sulfate, and filtered. The filtrate was freed from the solvent by distillation and the residue was recrystallized from chloroform/methanol to give 635 mg of monopyridylmethoxycalix[4]arene as a white powder. Yield : 59%, m.p.: 274.8° to 75.8° C.

|  | elemental analysis | | |
|---|---|---|---|
|  | C % | H % | N % |
| found | 80.41 | 8.29. | 1.80 |
| calculated | 81.15 | 8.31 | 1.89 |

Figure 6:
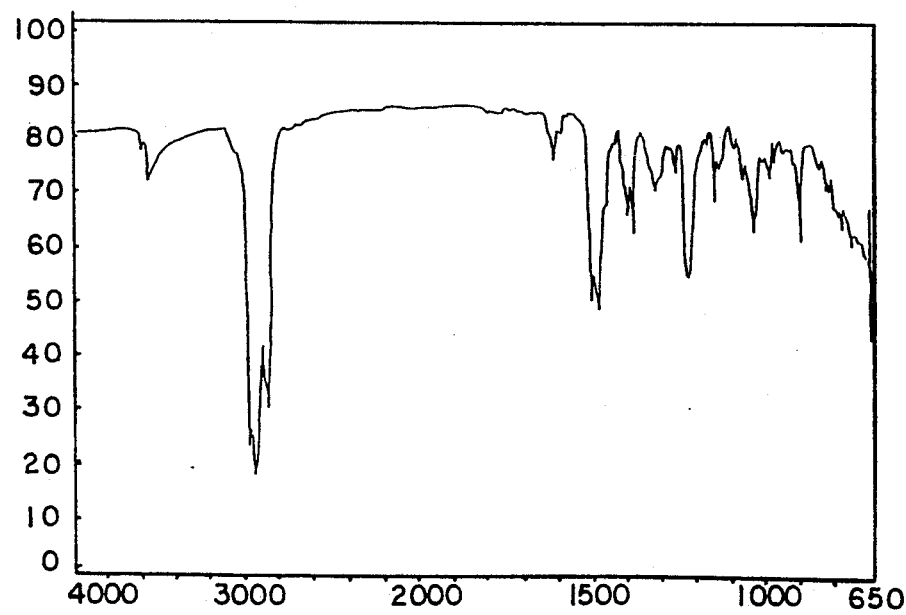
FIG. 6 is an infrared absorption spectrum of the calixarene derivative prepared in Example 2.
Figure 7:
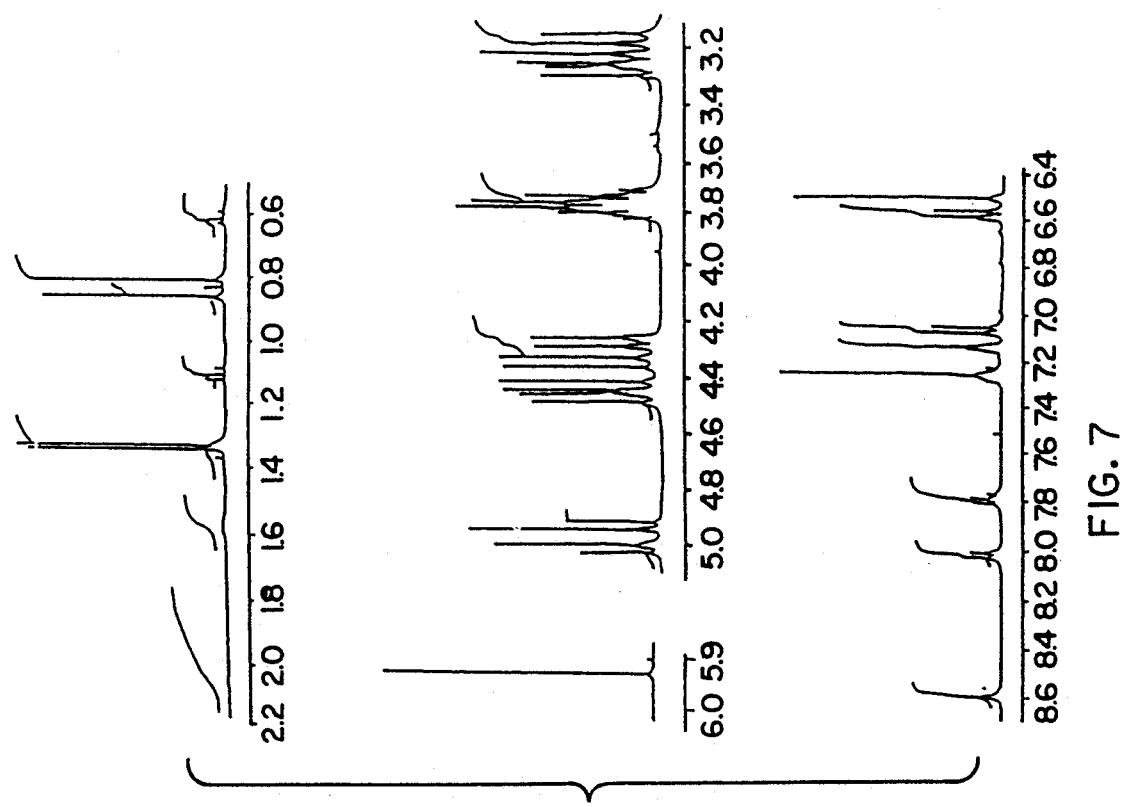
FIG. 7 is a nuclear magnetic resonance spectrum thereof.

2 g (2.70 mmol) of the above product, 3.36 g (10.65 mmol) of barium hydroxide octahydrate and 1.68 g (10.96 mmol) of barium oxide were suspended in 40 ml of dimethylformamide, followed by the addition of 1.33 g (10.8 mmol) of n-propyl bromide. The obtained mixture was stirred in an oil bath kept at 70° C. for 7 hours and extracted with chloroform/water. The chloroform layer was separated, washed with water, dried over anhydrous sodium sulfate, and filtered. The filtrate was freed from the solvent by distillation and the residue was recrystallized from methanol to give 2 g of the title compound as a white powder. Yield: 90%, m.p.: 170.0° to 171.5° C. The infrared absorption spectrum of the product is shown in FIG. 6 and the nuclear magnetic resonance spectrum thereof is shown in FIG. 7.

| | elemental analysis | | |
|---|---|---|---|
| | C % | H % | N % |
| found | 81.72 | 8.41 | 1.67 |
| calculated | 82.01 | 8.48 | 1.71 |

EXAMPLE 3

Figure 8:
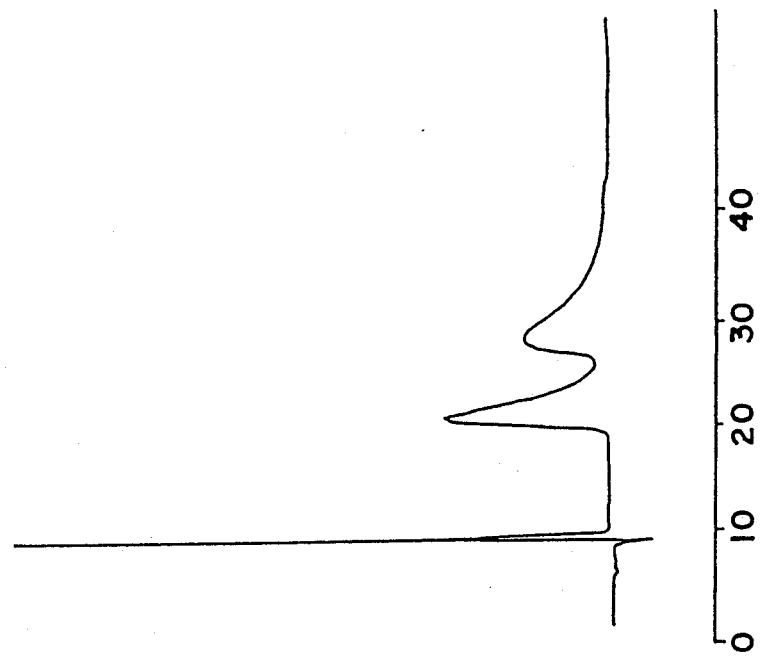
FIG. 8 is a chromatogram of the optical resolution in Example 3.

Optical resolution of 5,11,17-tri-t-butyl-22-methyl-23-isopropyl-25,26,27,28-tetra-n-propyloxycalix[4]arene The optical resolution was conducted by the use of Chiralpak OP (a product of Daicel Chemical Industries, Ltd.) connected to a high-performance liquid chromatograph, under the following conditions:
solvent: hexane/2-propanol/methanol=1/3/16,
flow rate: 0.4 ml/min,
temperature: room temperature,
detection: UV 254 nm.
The obtained chromatogram is shown in FIG. 8. The resolved optical isomers were separately recovered by the use of the same column as that used above. 35 mg of a nearly pure (+) isomer and 25 mg of a (−) isomer having an optical purity of 95% were obtained from 100 mg of the racemic modification.
The angle of rotation $[\alpha]_D$ of the (+) isomer was +255 (c=0.08, in chloroform). The circular dichroism spectra of the both isomers are shown in FIG. 9.

EXAMPLE 4

Optical resolution of 5,11,17,23-tetra-t-butyl-25-(2-pyridylmethoxy)-26,27-di-n-propyloxycalix[4]arene The above optical resolution was conducted by the use of Sumipax BOA-2000 (a product of Sumitomo Chemical, Co., Ltd.) connected to a high-performance liquid chromatograph, under the following conditions:
solvent: hexane/2-propanol=98/2,
flow rate: 2.0 ml/min,
temperature: room temperature,
detection: UV 254 nm.
The obtained chromatogram is shown in FIG. 10. The resolved optical isomers were separately recovered by the use of the same column as that used above. 50 mg of a nearly pure (+) isomer and 20 mg of a (−) isomer having an optical purity of 99.9% were obtained from 120 mg of the racemic modification. The angle of rotation $[\alpha]_D$ of the (+) isomer was +12.5 (c=0.04, in hexane). The circular dichroism spectra of both optical isomers are shown in FIG. 11.

What is claimed is:

1. An optically active calixarene derivative represented by the following general formula:

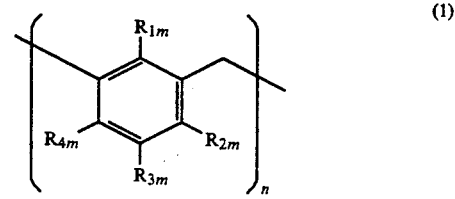

(1)

wherein n is an integer of 4 to 12; m is an integer of 1 to n; and $R_{11}$ to $R_{1m}$, $R_{21}$ to $R_{2m}$, $R_{31}$ to $R_{3m}$ and $R_{41}$ to $R_{4m}$ represent each a hydrogen atom, a straight-chain or branched, saturated or unsaturated, acyclic or cyclic group having 1 to 20 carbon atoms and which may contain a heteroatom, a substituted or unsubstituted aromatic group having 4 to 20 carbon atoms, or an aralkyl group having 5 to 20 carbon atoms, with the proviso that they be selected so as to be bulky enough to hinder the rotation of the benzene units.

2. The optically active calixarene derivative of claim 1, wherein said derivative is selected from the group consisting of 4-methyl-5-isopropyl-11,17,23-tri-t-butyl-25,26,27,28-tetra-n-propyloxycalix[4]arene, 5,11,17,23-tetra-t-butyl-25-(2-pyridylmethoxy)-26, 27-di-n-propyloxycalix[4]arene and 5,11,17-tri-t-butyl-22-methyl-23-isopropyl-25,26,27,28-tetra-n-propyloxycalix[4]arene.

3. The optically active calixarene derivative of claim 1, wherein n is 4 and $R_{11}$ to $R_{14}$ are a n-propyloxy group.

* * * * *

UNITED STATES PATENT AND TRADEMARK OFFICE
CERTIFICATE OF CORRECTION

PATENT NO. : 5 231 196
DATED : July 27, 1993
INVENTOR(S) : Seiji SHINKAI et al It is certified that error appears in the above-identified patent and that said Letters Patent is hereby corrected as shown below:

On the title page, item [75] Inventors:
    change "Kirosuke Kawabata" to ---Hirosuke Kawabata---.

Signed and Sealed this

Fifth Day of April, 1994

Attest:

BRUCE LEHMAN

*Attesting Officer*     *Commissioner of Patents and Trademarks*